United States Patent [19]
Causey, III

[11] Patent Number: 5,411,547
[45] Date of Patent: May 2, 1995

[54] IMPLANTABLE CARDIOVERSION-DEFIBRILLATION PATCH ELECTRODES HAVING MEANS FOR PASSIVE MULTIPLEXING OF DISCHARGE PULSES

[75] Inventor: James D. Causey, III, Simi Valley, Calif.

[73] Assignee: Pacesetter, Inc., Sylmar, Calif.

[21] Appl. No.: 104,295

[22] Filed: Aug. 9, 1993

[51] Int. Cl.⁶ .......................... A61N 1/39; A61N 1/05
[52] U.S. Cl. ........................................ 607/129; 607/5
[58] Field of Search ................ 128/642; 607/129, 130, 607/148, 152, 67, 74, 5

[56] References Cited

U.S. PATENT DOCUMENTS

| | | |
|---|---|---|
| D. 273,514 | 4/1984 | Heilman et al. ............... D24/29 |
| 4,030,509 | 6/1977 | Heilman et al. . |
| 4,291,707 | 9/1981 | Heilman et al. . |
| 4,314,095 | 2/1982 | Moore et al. ............... 174/84 C |
| 4,628,937 | 12/1986 | Hess et al. ............... 128/642 |
| 4,821,723 | 4/1989 | Baker, Jr. et al. ............... 607/129 X |
| 4,827,932 | 5/1989 | Ideker et al. . |
| 4,938,231 | 7/1990 | Milijasevic et al. . |

*Primary Examiner*—William E. Kamm
*Assistant Examiner*—Jeffrey R. Jastrzab
*Attorney, Agent, or Firm*—Lisa P. Weinberg; Malcolm J. Romano

[57] ABSTRACT

An apparatus for treating arrhythmias of the human heart includes a defibrillator, and an arrangement for providing passive diode multiplexing between two patches for bidirectionally passing an electric current through a human heart. The arrangement is formed by connecting a cathode of a first diode to a first mesh electrode on a first conductor and connecting an anode of a second diode to a second mesh electrode on the first patch. An anode of the first diode and a cathode of the second diode are then connected to a lead. An identical diode arrangement is provided for the second patch.

6 Claims, 2 Drawing Sheets

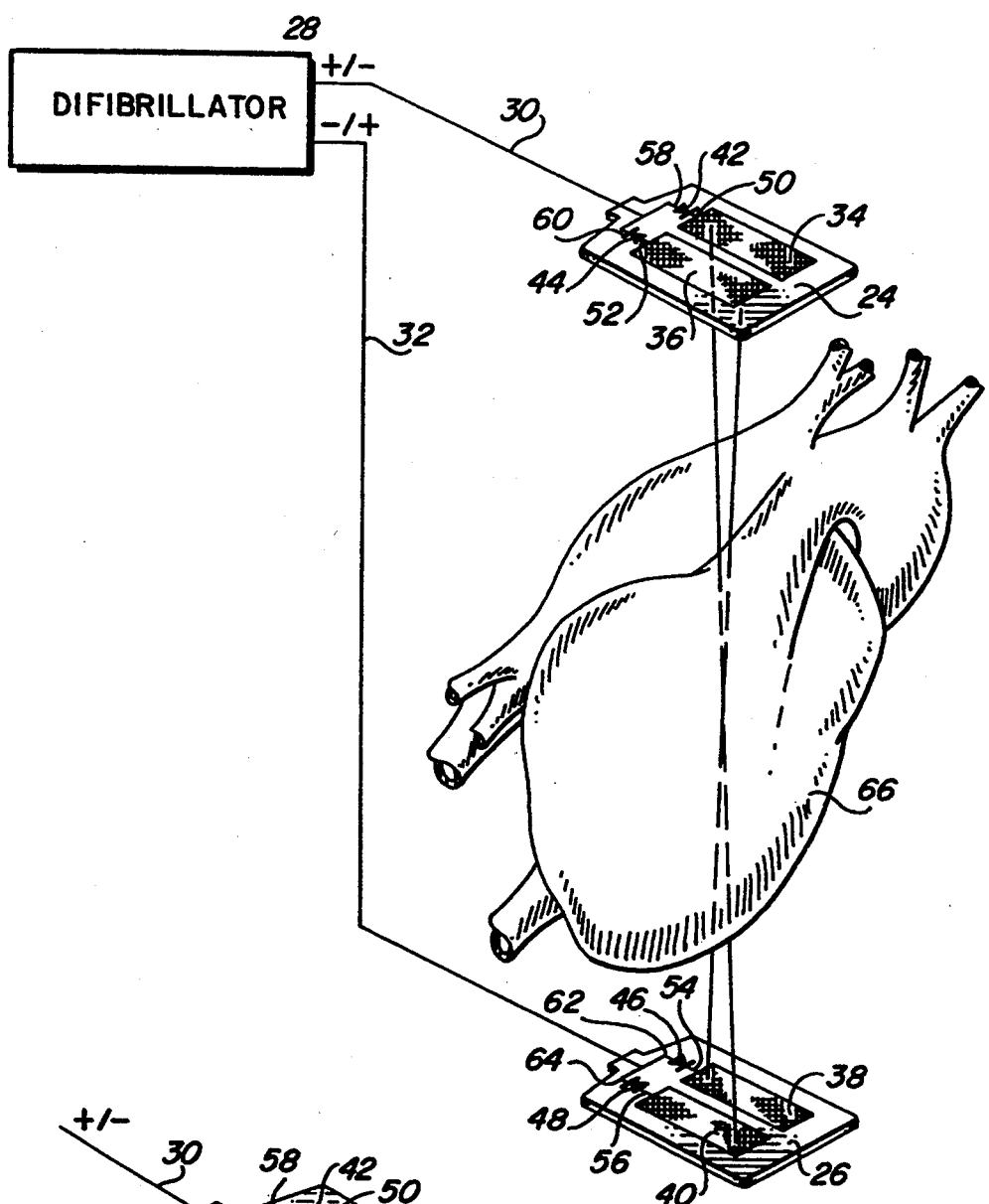
Fig. 4
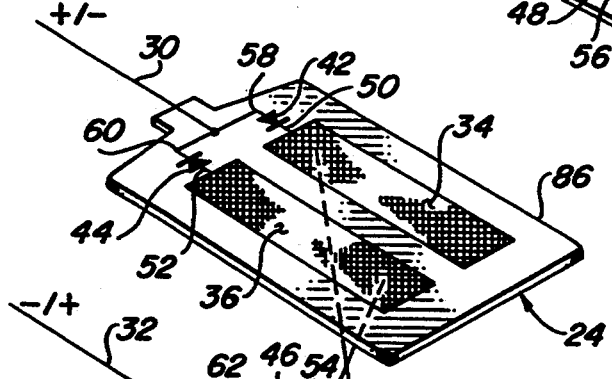
Fig. 3
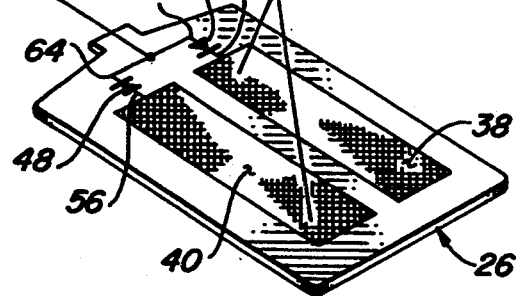

IMPLANTABLE CARDIOVERSION-DEFIBRILLATION PATCH ELECTRODES HAVING MEANS FOR PASSIVE MULTIPLEXING OF DISCHARGE PULSES

FIELD OF THE INVENTION

The present invention relates generally to electrodes for use in an implantable cardioversion-defibrillation electrodes.

BACKGROUND OF THE INVENTION

Implantable electrodes are used for cardioverting a human heart by applying electric shocks in vivo to the heart. A variety of arrhythmias of the heart can be treated internally with the use of implantable electrodes. Such arrhythmias can include, for example, atrial fibrillation, atrial flutter, atrial tachycardia, ventricular fibrillation, ventricular tachycardia, and asystole (a stopped heart). The term "defibrillation" or "defibrillating" as used herein, includes the term "cardioversion" and all other terms that denote a method of applying electric shocks to the human heart to treat such arrhythmias.

Typically, implantable electrodes are connected by leads to an implantable standby defibrillator. A typical defibrillator includes a capacitor. The capacitor is charged with and stores an electric charge capable of depolarizing a human heart when discharged across the implantable electrodes. The capacitor is connected in a discharge circuit, which is in turn connected to a sensing circuit. The system may also include a sensor for monitoring one or more physiological activities of the patient. The sensor is typically located in a transvenous pacing lead. When an arrhythmia of the heart is sensed, the capacitor is caused by the discharge circuit to discharge an electric shock which is delivered to the heart through two implantable electrodes.

Various shocking electrode configurations are known. One implantable shocking electrode may be positioned within the right ventricle or right atrium of the heart, with the distal tip of the transvenous lead being used for pacing. The other implantable shocking electrode may be positioned either directly on the ventricular myocardium or subcutaneously positioned along the interior chest wall.

Other known implantable shocking electrode configurations used in conjunction with implantable defibrillators employ electrodes which are all in contact with the exterior surface of the human heart.

The voltage levels and pulse sequences which will successfully terminate a particular tachycardia or fibrillation are not universal, and frequently a number of different combinations must be tried before the arrhythmia is successfully terminated. The voltage levels and pulse sequences may include various morphologies to include biphasic and/or monophasic waveforms. In all of the known implantable electrode systems, an electric current is discharged in a path across a first implantable electrode through the human heart to a second implantable electrode. Therefore, such polarity reversals must be undertaken in an electronic multiplexer containing in the implantable housing, or additional electrodes must be provided. The first approach occupies additional space and consumes additional energy, both of which are undesirable, and the second approach requires more extensive surgery than would otherwise be necessary.

SUMMARY OF THE INVENTION

The present invention includes an implantable apparatus for treating arrhythmias of the human heart including a pair of patches that bidirectionally shock the human heart with an electric current using passive diode multiplexing.

Each patch includes of a pair of mesh electrodes coupled through a pair of diodes, respectively, to a single conductor. A first diode is configured in a "forward" direction relative to the conductor. A second diode is configured in a "reverse" direction relative to the conductor.

When a stimulation pulse is generated, a voltage will develop across the two patches which will allow current to flow through the tissue from the first patch to the second patch and then back from the second patch to the first patch (i.e., bidirectionally).

More specifically, when the first diode is forward biased and conducts, current will flow from the first electrode on the first patch, through the tissue, to the first electrode on the second patch. The current will then be directed by both diodes on the second patch to allow current to flow from the first electrode on the second patch to the second electrode on the second patch. The current will then flow through the tissue in the opposite direction and back to the second electrode on the first patch. If there is any remaining charge after one cycle, the current will continue to bidirectionally cycle through the tissue until it has dissipated.

Advantageously, the patches cannot be incorrectly connected to the cardioverting/defibrillator system, since the steering diodes will also work in the reverse direction.

Thus, in accordance with the principles of the present invention, an electric shock can be delivered to a human heart in a bidirectional fashion across a pair of patches, rather than unidirectionally shocking the heart with a known electrode system in order to treat an arrhythmia of the heart.

Other advantages and features of the invention will be readily apparent from the following description of the preferred embodiments, the drawings and claims.

DESCRIPTION OF THE DRAWINGS

FIG. 3 illustrates a preferred embodiment of a patch electrode configuration constructed in accordance with the principles of the present invention; and FIG. 4 illustrates an implantable system employing patch electrodes constructed in accordance with the principles of the present invention.

DETAILED DESCRIPTION OF THE PREFERRED EMBODIMENTS

Figure 1:
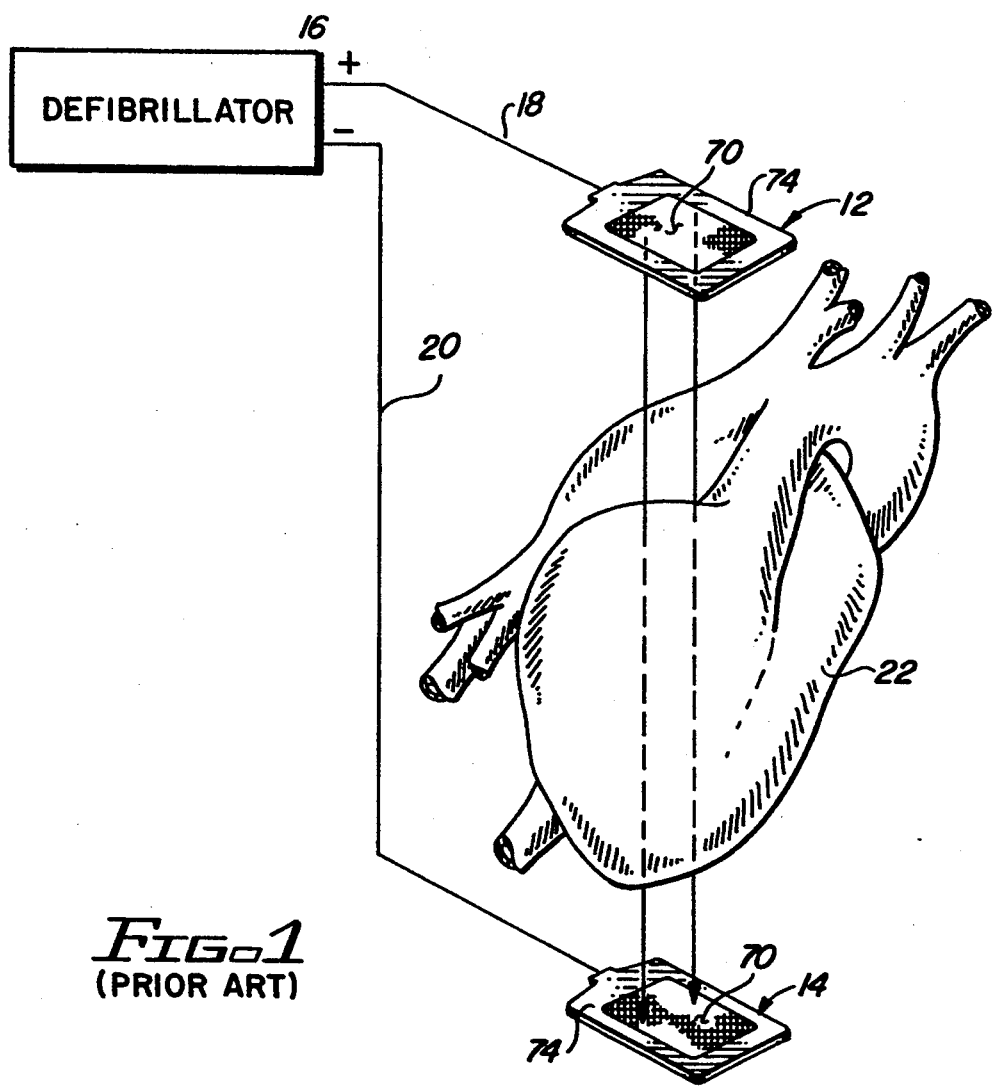
FIG. 1 illustrates an implantable stimulation system of the prior art.

FIG. 1 illustrates an implantable stimulation system 10 of the prior art. First and second implantable electrodes 12 and 14 are provided. The first and second implantable electrodes 12 and 14 are respectively connected to a known tissue stimulator, such as a defibrillator 16, through leads 18 and 20. When a capacitor (not illustrated) of the defibrillator 16 is discharged, an electric shock is delivered to the first implantable electrode 12 through lead 18 and traverses through the heart 22 to the second implantable electrode 14. Thus, a unidirectional electric shock is delivered to the heart by the known implantable electrode configuration 10.

Figure 2:
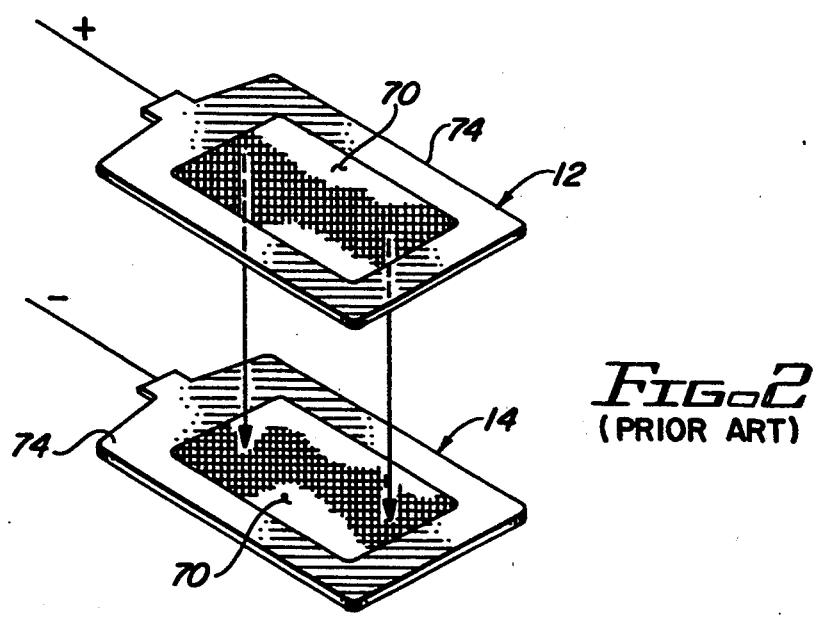
FIG. 2 illustrates an implantable electrode configuration, shown in FIG. 1, wherein the electrodes are formed of a metal mesh as is known in the prior art.

FIG. 2 illustrates further details of the prior art implantable patch electrode configuration of FIG. 1. Patch electrodes 12 and 14 are formed of a metal mesh 70 and surrounded by a continuous border 74.

FIG. 3 illustrates an implantable electrode configuration constructed in accordance with the principles of the present invention. First and second patches 24 and 26 are provided. The first and second patches 24 and 26 are respectively connected to a known defibrillator (shown as 28 in FIG. 4) through leads 30 and 32. Four mesh electrodes 34, 36, 38, and 40 provide a current path through a passive diode multiplexing arrangement, comprised of diodes 42, 44, 46, and 48.

A cathode 50 of diode 42 is connected to the first mesh electrode 34. An anode 52 of diode 44 is connected to the second mesh electrode 36. Similarly, a cathode 54 of diode 46 is connected to the third mesh electrode 38, and an anode 56 of the fourth diode 48 is connected to the fourth mesh electrode 40.

An anode 58 of diode 42 and a cathode 60 of diode 44 are connected to lead 30. Similarly, an anode 62 of diode 46 and a cathode 64 of diode 48 are connected to lead 32. Preferably, general purpose forward-biased diodes are used in the passive multiplexing arrangement.

As illustrated in FIGS. 3 and 4, when a capacitor (not shown) in the defibrillator 28 discharges, an electric current traverses the lead 30 and through diode 42 to the first mesh electrode 34. The electric shock then traverses through the heart 66 to mesh electrode 40. The electric current then proceeds through diodes 48 and 46 to mesh electrode 38. The electric current then proceeds through the heart 66 to mesh electrode 36 and then through diodes 44 and 42 to the first mesh electrode 34. Thus, passive diode multiplexing is achieved, and the four mesh electrodes formed by the passive diode multiplexing arrangement provide bidirectional electric shocks through the heart 66.

Exposed electrodes 34, 36, 38 and 40 are formed of a metal mesh surrounded by a continuous border 86 and 88 of insulating material. Each patch contains two mesh electrodes (34 and 36, or 38 and 40). The metal mesh can be formed of any suitable metal or a combination of metals, such as MP-35 stainless steel, titanium, or platinum.

The electrodes 34, 36, 38 and 40 can be used as conformal electrodes (in direct contact with the heart), or can be arranged near the surface of the heart 66 (illustrated in FIG. 1). The patch electrodes 34, 36, 38 and 40 can be suitably arranged in an anterior-anterior or anterior-posterior position.

Another advantage of this system is that the electrodes cannot be connected incorrectly to the implantable defibrillation device. That is, if the patch electrodes 26 and 24 are connected to the positive and negative terminals, respectively, then the current would flow from the lead 32 through diode 46 to the mesh electrode 38. The electric shock would traverse the heart 66 to mesh electrode 36. The electric current would then proceed through diodes 44 and 42 to mesh electrode 34. The electric current would then proceed back through the heart 66 to mesh electrode 40.

Although various minor modifications may be suggested by those versed in the art, it should be understood that I wish to embody within the scope of the patent granted hereon all such modifications as reasonably and properly come within the scope of my contribution to the art.

What is claimed is:

1. A shocking electrode system comprising:
   implantable cardioverter-defibrillator means for providing bidirectional shocking pulses;
   a first and a second patch lead for delivering shocking pulses to selected cardiac tissue, the first and second patch lead including means for electrically interfacing with the implantable cardioverter-defibrillator means, the first and second patch lead further including:
   bidirectional switching means for directing a current associated with a shocking pulse in a first direction from the first patch lead through the cardiac tissue to the second patch lead, and in a second direction from the second patch lead through the cardiac tissue to the first patch lead, wherein each one of the first and second patch leads comprises:
   an insulated conductor; and
   a patch area, coupled to the conductor, having a conductive surface and a nonconductive surface, the conductive surface being adapted to be disposed toward the cardiac tissue and the nonconductive surface being adapted to be disposed away from the cardiac tissue, the conducting surface having a first and a second mesh electrode mounted thereon.

2. The shocking electrode system, as recited in claim 1, wherein the bidirectional switching means comprises four diodes, a first and a second diode being mounted onto the first patch, and a third and a fourth diode being mounted onto the second patch.

3. The shocking electrode system, as recited in claim 2, wherein:
   the first diode has a cathode connected to the first mesh electrode on the first patch; and
   the second diode has an anode connected to the second mesh electrode on the first patch; and
   wherein an anode of the first diode and a cathode of the second diode are connected to the conductor of the first patch.

4. The shocking electrode system, as recited in claim 3, wherein:
   the third diode has a cathode connected to the first mesh electrode on the second patch; and
   the fourth diode has an anode connected to the second mesh electrode on the second patch; and
   wherein an anode of the third diode and a cathode of the fourth diode are connected to the conductor for the second patch.

5. A shocking electrode for providing bidirectional current flow comprising:
   a patch having first and second mesh electrodes thereon; and
   diode multiplexing means electrically coupled to the first and second mesh electrodes for steering current flow in a first direction through the first mesh electrode and for steering the current flow in a direction opposite to the first direction through the second mesh electrode.

6. The shocking electrode, as recited in claim 5, further comprising a lead electrically coupled to the patch wherein the diode multiplexing means comprises:
   a first diode having a cathode connected to the first mesh electrode; and
   a second diode having an anode connected to the second mesh electrode,
   wherein an anode of the first diode and a cathode of the second diode are connected to the lean.

* * * * *